(12) United States Patent
Motoda et al.

(10) Patent No.: US 7,195,895 B2
(45) Date of Patent: Mar. 27, 2007

(54) METHOD OF PRODUCING TEMPLATE DNA AND METHOD OF PRODUCING PROTEIN IN CELL-FREE PROTEIN SYNTHESIS SYSTEM USING THE SAME

(75) Inventors: Yoko Motoda, Yokohama (JP); Takashi Yabuki, Yokohama (JP); Takanori Kigawa, Yokohama (JP); Shigeyuki Yokoyama, Yokohama (JP)

(73) Assignee: Riken, Wako (JP)

( * ) Notice: Subject to any disclaimer, the term of this patent is extended or adjusted under 35 U.S.C. 154(b) by 0 days.

(21) Appl. No.: 10/748,055

(22) Filed: Dec. 31, 2003

(65) Prior Publication Data

US 2004/0214292 A1 Oct. 28, 2004

(30) Foreign Application Priority Data

Jul. 2, 2001 (JP) .............................. 2001-201356
Jun. 24, 2002 (WO) ....................... PCT/JP02/06261

(51) Int. Cl.
    *C12P 19/34* (2006.01)
(52) U.S. Cl. ..................................... 435/91.2; 435/488
(58) Field of Classification Search .................... 435/6, 435/68.1, 91.1, 91.5; 536/24.3, 25.3
    See application file for complete search history.

(56) References Cited

U.S. PATENT DOCUMENTS

| 5,800,984 | A | 9/1998 | Vary |
| 6,136,568 | A | 10/2000 | Hiatt et al. |
| 6,303,337 | B1 * | 10/2001 | Rothschild et al. ........ 435/69.1 |
| 2002/0025525 | A1 | 2/2002 | Shuber |
| 2003/0050453 | A1 * | 3/2003 | Sorge ......................... 536/23.1 |
| 2004/0121346 | A1 * | 6/2004 | Endo et al. ..................... 435/6 |

FOREIGN PATENT DOCUMENTS

| EP | 0 469 610 A1 | 2/1992 |
| EP | 1 316 616 A1 | 6/2003 |
| JP | 09-234074 A | 9/1997 |
| JP | 04-91790 A | 3/2004 |
| WO | WO92-07949 | * 5/1992 |
| WO | WO 97/46696 | * 12/1997 |
| WO | WO99-57992 | * 11/1999 |
| WO | WO-00/56914 A1 | 9/2000 |
| WO | WO 02/18586 A1 | 3/2002 |

OTHER PUBLICATIONS

Kigawa et al, Tanpakushitsu Kakusan Koso., 2002, vol. 47, No. 8, pp. 1014 to 1019 and complete English language translation.

Kain, et al.; "Universal Promoter for Gene Expression Without Cloning: Expression-PCR"; BioTechniques; vol. 10, No. 3; Mar. 1991; pp. 366-368 and 370; XP-000912135.

Macferrin, et al.; "Overproduction and Dissection of Proteins by the Expression-Cassette Polymerase Chain Reaction"; Proceedings of the National Academy of Sciences of the USA; Mar. 1, 1990; vol. 87, No. 5; pp. 1937-1941; XP000268593.

Ohuchi, et al.; "*In Vitro* Method for the Generation of Protein Libraries Using PCR Amplification of a Single DNA Molecule and Coupled Transcription/Translation"; Nucleic Acids Research; Oct. 1998; vol. 26, No. 19; pp. 4339-4346; XP-002119037.

Nakano, et al.; "Efficient Coupled Transcription/Translation From PCR Template by a Hollow-Fiber Membrane Bioreactor"; Biotechnology and Bioengineering, Interscience Publishers; Jul. 20, 1999; XP-001084028; pp. 194-199.

Sandhu, et al.; "Dual Asymmetric PCR: One-Step Construction of Synthetic Genes"; Biotechniques; vol. 12, No. 1; 1992; XP-002134139; pp. 14-16.

Ge, et al. ; "Simultaneous Introduction of Multiple Mutations Using Overlap Extension PCR"Biotechniques, vol., 22, No. 1, Jan. 1997; XP-000676361; pp. 28 and 30.

Horton, et al.; "Engineering Hybrid Genes Without the Use of Restriction Enzymes: Gene Splicing by Overlap Extension"; GEne, Elsevier Biomedical Press; vol. 77; Apr. 15, 1989; pp. 61-68; XP-002090392.

\* cited by examiner

*Primary Examiner*—James Ketter
(74) *Attorney, Agent, or Firm*—Birch, Stewart, Kolasch & Birch, LLP

(57) ABSTRACT

Provided is a method of producing a template DNA used for protein synthesis comprising a step of amplifying a linear double-stranded DNA by polymerase chain reaction (PCR), by using a reaction solution comprising a first double-stranded DNA fragment comprising a sequence coding for a protein or a portion thereof, a second double-stranded DNA fragment comprising a sequence overlapping with the 5' terminal region of the first DNA fragment, a third double-stranded DNA fragment comprising a sequence overlapping with the 3' terminal region of the first DNA fragment, a sense primer which anneals with the 5' terminal region of the second DNA fragment, and an anti-sense primer which anneals with the 3' terminal region of the third DNA fragment, wherein the second DNA fragment comprises a regulatory sequence for transcription and translation of a gene, and the concentrations of the second DNA fragment and the third DNA fragment in the reaction solution each range from 5 to 2,500 pmol/L. The use of this method enables efficient production of a template DNA for expression and purification of a protein.

15 Claims, 5 Drawing Sheets

Tags

1: 1st PCR product
2: His tag
3: native His
4: GST
5: MBP
6: CBD
7: TrxA

2nd PCR product

US 7,195,895 B2

METHOD OF PRODUCING TEMPLATE DNA AND METHOD OF PRODUCING PROTEIN IN CELL-FREE PROTEIN SYNTHESIS SYSTEM USING THE SAME

This Nonprovisional application claims priority under 35 U.S.C. § 119(a) on Patent Application No(s). 2001-201356 filed in JAPAN on Jul. 2, 2001, and PCT International Application No. PCT/JP02/06261 filed on Jun. 24, 2002, which designated the United States, and on which priority is claimed under 35 U.S.C. § 120, the entire contents of which are hereby incorporated by reference.

TECHNICAL FIELD

The present invention relates to a method of producing a template DNA for protein synthesis and a method of producing a protein using a template DNA that is produced by the method.

BACKGROUND ART

Regarding a huge number of genes derived from a great deal of genomic sequence information of organisms, a research called "Structural Genomics" is now in progress, which is a systematic and comprehensive analysis of the relationship between structure and function of proteins by determining three dimensional structures of the proteins encoded by the respective genes. As the total genome sequences were clarified, it was found that three-dimensional protein structures considered to be innumerable actually comprise combinations of one to several thousands of basic structures (folds) and these combinations seem likely to realize the diversity of functions. Accordingly, high-throughput technologies throughout the processes from synthesis to structural analysis of proteins will make it possible to reveal all of the basic structures of the proteins and based on the knowledge of the basic structures, it will be enabled to elucidate the relationship between structure and function of the proteins.

As a system for expressing and preparing a number of protein samples at good efficiency, cell-free protein synthesis systems have been improved by various modifications such as introduction of dialysis, to obtain proteins in the order of milligrams within several hours (refer to Kigawa et al., FEBS Lett., vol. 442, pp. 15–19, 1999 and Japanese Patent Kokai publication JP-A-2000-175695). To express proteins in this cell-free protein synthesis system at good efficiency, a double-stranded DNA containing an appropriate expression regulatory region and a gene sequence coding for a target protein to be expressed is needed as a template DNA. In order to express any genes cloned in a cloning vector free of an appropriate expression regulatory sequence in a cell-free protein synthesis system, it is necessary to add an appropriate expression regulatory sequence to these genes. Therefore, several methods have been so far performed, in which a desired DNA fragment is excised from a plasmid vector comprising a gene by restriction enzymes or PCR amplification, then re-cloned in a vector having an appropriate expression regulatory sequence, or a desired DNA fragment was further amplified by PCR.

To obtain a highly efficient protein expression, it is required to promote the transcription of the gene with strong promoter or terminator sequence as well as to enhance the translation by improving the affinity between mRNA and ribosomes. Further, for quickly purifying or detecting synthesized proteins, it is also required to design fusion proteins having incorporated therein a tag sequence for affinity purification or detection.

When the template DNA suitable for such protein synthesis is prepared, however, much expense in time and effort is necessary to clone the DNA by genetic engineering techniques using living cells such as *E. coli*, because the methods are complicated and difficult to make high-throughput by automation. It is also problems to construct the template DNA by complex recombination, or to synthesize many kinds of primers for PCR for the optimization of respective genes.

DISCLOSURE OF THE INVENTION

It is therefore an object of the present invention to provide an efficient method of preparing a template DNA to express and purify a protein.

In view of the foregoing aim, the present inventors have assiduously conducted investigations on a method of producing a template DNA in a cell-free protein synthesis system, and have consequently found that a linear template DNA appropriate for expression of a protein can be synthesized very quickly and efficiently by amplifying an optional cloned DNA selected from cDNA library through 2-step PCR. This finding has led to the completion of the invention.

In the first aspect of the present invention, there is provided a method of producing a template DNA used for protein synthesis comprising a step of:

amplifying a linear double-stranded DNA by polymerase chain reaction (PCR), using a reaction solution comprising, a first double-stranded DNA fragment comprising a sequence coding for a protein or a portion thereof, a second double-stranded DNA fragment comprising a sequence overlapping with the 5' terminal region of the first DNA fragment, a third double-stranded DNA fragment comprising a sequence overlapping with the 3' terminal region of the first DNA fragment, a sense primer which anneals with the 5' terminal region of the second DNA fragment, and an anti-sense primer which anneals with the 3' terminal region of the third DNA fragment, wherein the second DNA fragment comprises a regulatory sequence for transcription and translation of a gene, and the concentrations of the second DNA fragment and the third DNA fragment in the reaction solution each range from 5 to 2,500 pmol/L.

In a preferred embodiment, the invention is characterized in that the reaction solution (second PCR solution) comprises first PCR products obtained by polymerase chain reaction (first PCR) to amplify the first double-stranded DNA fragment, and the respective concentrations of primers remaining in the first PCR products and primer dimers produced in the first PCR are less than 20 nmol/L in the second PCR solution.

Thus, the invention is characterized in that for decreasing the amounts, incorporated into the second PCR, of primers used in the first PCR and primer dimers produced as byproducts, the concentrations of the primers used for the first PCR are in the range of from 20 to 500 nmol/L, or the second PCR is performed with the first PCR products which are diluted to 10- to 100-fold (at a final concentration in the second PCR solution), or both of these are performed in combination, or the second PCR is performed after removing the primers and the primer dimers from the first PCR solution.

In one embodiment, the invention is characterized in that the first PCR is carried out using recombinant microorganisms or a culture broth thereof comprising the first double-stranded DNA fragment.

In another preferred embodiment, the invention is characterized in that the sense primer and the anti-sense primer have the same nucleotide sequence, and/or the second DNA fragment comprises a transcription termination sequence.

In the other preferred embodiment, the invention is characterized in that at least one of the second DNA fragment and the third DNA fragment comprises a sequence coding for a tag peptide, and the tag peptide is synthesized by being fused with the protein or a portion thereof. The tag peptide is preferably maltose binding protein, cellulose binding domain, glutathione-S-transferase, thioredoxin, streptavidin binding peptide or histidine tag peptide.

The invention provides, in another aspect, a method of producing a protein in a cell-free protein synthesis system, characterized by using a template DNA that is produced by any of the foregoing methods.

PREFERRED EMBODIMENT OF THE INVENTION

Figure 1:
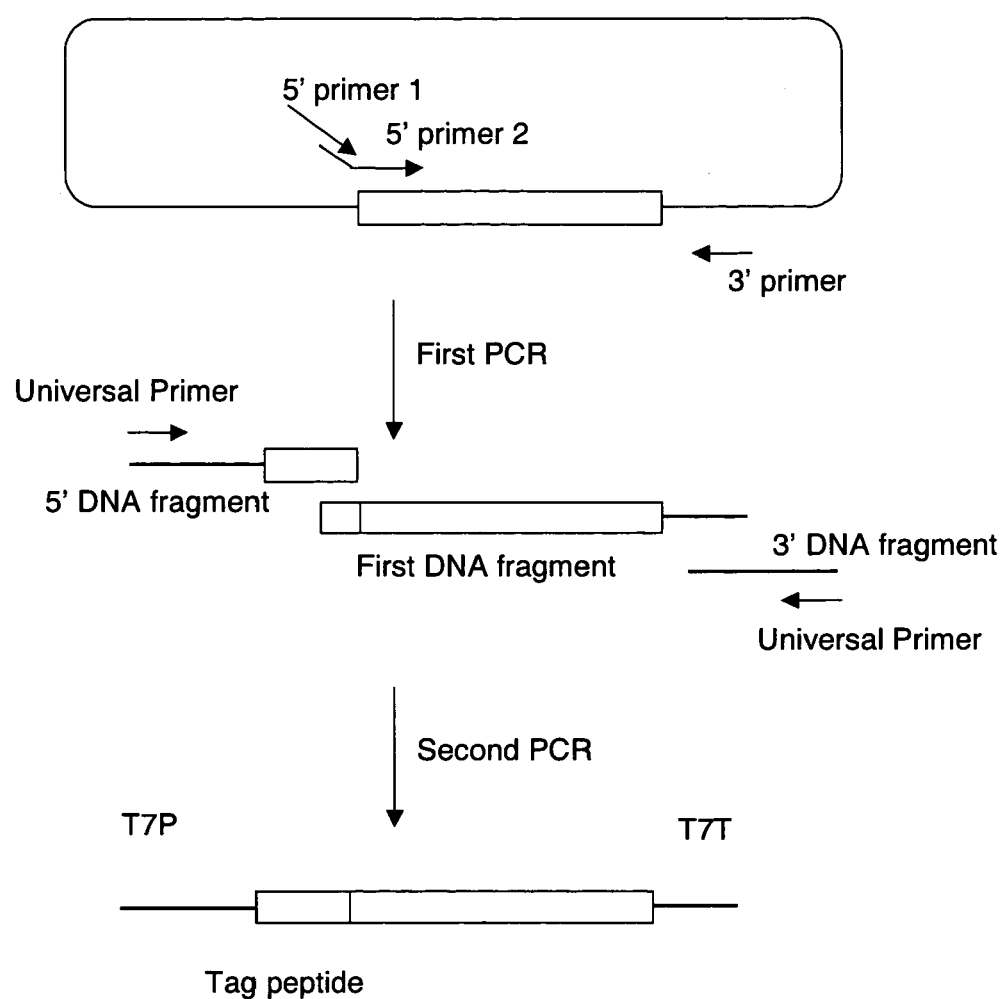
FIG. 1 is a flow chart showing a method of producing a linear template DNA, which is one embodiment of the present invention.

One embodiment of the present invention is described in detail below along the attached drawings. FIG. 1 is a flow chart showing a method of producing a linear double-stranded template DNA for protein synthesis by 2-step PCR using a plasmid DNA with a full-length cDNA cloned.

(1) First PCR

With respect to the template DNA of the first PCR, any template DNA will be used, so long as it comprises a sequence coding for a desired protein. For example, not only a DNA cloned from cDNA library but also a genomic DNA clone or a synthetic DNA can be used. Further, an unpurified DNA is also available. For example, a strain carrying a plasmid vector comprising the foregoing sequence or a culture broth of the strain can be used. FIG. 1 shows modified bluescript 1 which is a plasmid obtained by cloning mouse full-length cDNA in SacI and XhoI sites of plasmid vector pBLUESCRIPT SK+.

In FIG. 1, two primers (5'-primer 1 and 5'-primer 2) are used as 5'-primers for amplifying a protein code region of a cloned cDNA. A nucleotide sequence of the 5'-primer 2 is designed to anneal with a nucleotide sequence corresponding to an amino terminal region of the protein encoded by the cloned cDNA. The 5'-primer 2 can further contain an arbitrary nucleotide sequence in the 5'-terminal side. Meanwhile, the 5'-primer 1 may have a sequence common to a part of the 5'-terminal side of the 5'-primer 2, and both of the primers overlap to function as the 5'-primers of the first PCR.

On the other hand, in FIG. 1, the 3'-primer is designed to anneal with a region of the plasmid vector where is located in the 3' downstream of the protein coding region, and elongates the DNA chain by PCR together with the 5'-primers to amplify the first DNA fragment coding for the protein to be expressed. Since the first DNA fragment is used as a template of the second PCR to be described later, it can be purified from the PCR reaction solution by a known method, or the PCR reaction solution can also be used directly. In this case, the primers remaining in the reaction solution might inhibit the second PCR reaction. For this reason, it is preferable that the amounts, incorporated into the second PCR solution, of primers used in the first PCR and primer dimers produced as byproducts in the first PCR are decreased to less than 20 nmol/L. Specifically, when plural primers are used as the 5'-primer or the 3'-primer, they are preferably used at a total concentration of from 20 to 500 nmol/L, more preferably from 50 to 100 nmol/L.

Alternatively, the amounts, incorporated into the second PCR, of the primers and the primer dimers can be reduced by diluting the first PCR solution to 10- to 100-fold.

Besides such methods, PCR using various primers is possible for obtaining the first DNA fragment. With respect to nucleotide sequences of primers, PCR reaction conditions and the like employed at that time, ordinary ones are available, and it is desirable to properly determine them by those skilled in the art. It is further possible to obtain the first DNA fragment by excising a DNA fragment directly from the cDNA clone with a restriction enzyme or the like.

(2) Second PCR

Next, the double-stranded second DNA fragment (hereinafter sometimes referred to as "5' DNA fragment") comprising a sequence overlapping with the 5' terminal region of the first DNA fragment is prepared. The second DNA fragment overlaps with the 5' terminal region of the first DNA fragment in its 3' terminal region, whereby these two DNA fragments mutually become primers and a template to allow an elongation reaction, producing a template DNA in the second PCR. The overlapping region is preferably at least 12 base pairs, more preferably at least 17 bases.

Subsequently, the double-stranded third DNA fragment (hereinafter sometimes referred to as "3' DNA fragment") comprising a sequence overlapping with the 3' terminal region of the first DNA fragment is produced. The third DNA fragment overlaps with the 3' terminal region of the first DNA fragment in its 5' terminal region, whereby these two DNA fragments mutually become primers and a template to allow an elongation reaction, producing a template DNA in the second PCR. The overlapping region is preferably at least 12 base pairs, more preferably at least 17 bases.

Then, as the primers for the second PCR, the sense primer which anneals with the 5' terminal region of the 5' DNA fragment and the anti-sense primer which anneals with the 3' terminal region of the 3' DNA fragment are synthesized. These primers may anneal with the template DNA of the second PCR to allow a DNA elongation reaction and amplify a desired DNA fragment. Plural primers that anneal with the both terminal regions of the template DNA can be used. Preferably, when the both terminal sequences are complementary nucleotide sequences, an amplification reaction is possible with one type of a primer (universal primer) as shown in FIG. 1. This primer usually comprises a single-stranded oligonucleotide of from 5 to 50 bases, preferably a single-stranded oligonucleotide of from 15 to 25 bases. The use of one type of a universal primer is more advantageous than the use of two types of primers because byproducts are less formed by PCR.

Generally, it is known that byproducts (primer dimers) in which primers are paired are formed by PCR. In case of using two types of primers, primer dimers once formed serve as a template DNA to amplify the byproducts and decrease amounts of primers used for amplification of a desired product. Consequently, an amount of a desired product is considered to be decreased. Meanwhile, when PCR is performed using only one type of a primer, it is considered that the resulting primer dimers tend to take a hairpin structure because they have complementary sequences in the same molecule, and are therefore less amplified by PCR to less form byproducts.

The 5' DNA fragment contains sequences of inducing and regulating transcription and translation of a gene in the upstream of the region overlapping with the first DNA fragment. The sequences of inducing and regulating the transcription of the gene are called promoter and operator sequences, and they have been studied in detail in prokaryotic cells and eukaryotic cells such as *Escherichia coli* and yeasts. For example, T7 promoter derived from a phage of *Escherichia coli* is used. It is known that in T7 promoter, potent transcription is performed with T7 RNA polymerase. Translation of an mRNA into a protein is induced by binding a translation initiation complex of a ribosome or the like to an mRNA. A ribosome binding sequence (RBS) is called an SD sequence, and important for efficient expression of a protein.

Further, these expression regulatory sequences contain, in the upstream, the sequence with which the sense primer anneals in PCR. The nucleotide sequence of the sense primer here may be one which serves as a primer by being hybridized with the 5' terminal region of the 5' DNA fragment, and it includes one in which one or more bases in the sequence complementary to the template DNA are deleted, substituted or added.

Likewise, the 3' DNA fragment contains, in the 3' terminal region, the sequence with which the anti-sense primer anneals in PCR. The anti-sense primer may be one which serves as a primer by being hybridized with the 3' terminal region of the 3' DNA fragment, and it includes one in which one or more bases in the sequence complementary to the template DNA are deleted, substituted or added.

The concentrations of the 5' DNA fragment and the 3' DNA fragment in the reaction solution of the second PCR are preferably lower than the concentrations of primer DNAs in usual PCR, and they are used at concentrations of from 5 to 2,500 pmol/L, preferably from 10 to 500 pmol/L. When the concentrations of these DNA fragments are higher than 2,500 pmol/L, byproducts tend to be formed during PCR. That is, single-stranded DNAs produced from the universal primer bound to the 5' DNA fragment and the 3' DNA fragment are bound in the same manner as the foregoing primer dimers, with the result that byproducts in which the 5' DNA fragment and the 3' DNA fragment are directly bound tend to be formed. The reason is that since these byproducts are shorter than the desired products, they tend to be amplified by PCR, act as a template that expresses only short proteins in the protein synthesis, and have therefore an adverse effect on the protein synthesis.

Meanwhile, when the concentrations of the DNA fragments are lower than 5 pmol/L, the amount of a DNA that serves as a template itself is decreased, and a sufficient amount of a desired DNA is not amplified. The other reaction conditions of the second PCR can properly be selected and used by those skilled in the art.

It is preferable that the 3' DNA fragment further comprises a transcription termination sequence. The transcription termination sequence is a DNA sequence of prompting separation of an RNA polymerase, and it has generally a characteristic structure of a symmetrical sequence enriched in GC and followed by T to allow an efficient transcription reaction.

The second PCR can be performed even with one or both of the 5' DNA fragment and the 3' DNA fragment being single-stranded DNA(s) instead of the double-stranded DNA(s), and this embodiment is also included in the scope of the invention.

(3) Tag Peptide

It is preferable that at least one of the 5' DNA fragment and the 3' DNA comprises a sequence coding for a tag peptide. The tag peptide is an amino acid sequence added to an N terminal and/or a C terminal of a protein to be expressed, and this is a sequence as a mark in affinity purification or western blotting detection of the protein. Examples thereof include glutathione-S-transferase (GST), maltose binding protein (MBP), thioredoxin (TrxA), cellulose binding domain (CBD), streptavidin binding peptide (for example, Streptag (trademark)) and histidine tag peptide.

Glutathione-S-transferase (GST) is a soluble enzyme protein. When a desired gene is incorporated in the downstream of this gene sequence by adapting the frame thereto, a fusion protein with GST can be expressed. Recombinant vectors, PGEX Vectors for this purpose are commercially available from Amersham Pharmacia Biotech. It is used for affinity purification or enzymatic immunostaining by utilizing an antibody that specifically recognizes a protein portion of GST or a property of binding to glutathione.

The maltose binding protein (MBP) is maltose binding protein of *Escherichia coli*. A fusion protein with MBP can be adsorbed on amylose or agarose gel, then separated with excess maltose and purified. Further, anti-MBP antibody can also be used.

Thioredoxin (TrxA) is a protein of *Escherichia coli* that catalyzes a redox reaction, and can be purified by metal chelate affinity chromatography with a pair of functional thiol groups. As a carrier for this purpose, for example, ThioBond (trademark) Resin (manufactured by Invitrogen) is commercially available.

The cellulose binding domain (CBD) is a cellulose binding domain sequence derived from *Clostridium cellulovorans* and *Cellulomonasfini*, and has a property of specifically binding to cellulose. It can be immobilized on an inert carrier such as cellulose or chitin without chemical modification.

As the streptavidin binding peptide, for example, a peptide made of 8 amino acids, called Strep-tag II, is known, and it can be purified by being bound selectively to Strep-Tactin (trade mark) or Streptavidine (trademark).

As the histidine tag, a peptide comprising at least 6 histidines which are located continuously or in close proximity is preferable. The protein encoded by the first DNA fragment is bound to this histidine tag either directly or through an amino acid sequence. The histidine tag has a high affinity for a divalent metallic atom, especially, a nickel atom. Accordingly, the protein having the histidine tag is firmly bound to a nickel affinity matrix and can easily be purified.

In an especially preferable embodiment, the histidine tag has an amino acid sequence described in SEQ ID No. 1. This sequence is a natural sequence (native His tag) derived from an N terminal of a lactic acid hydrogenase of a chicken muscle. Since the 6 histidine residues being basic amino acids are present by being properly separated, this is advantageously lower in isoelectric point than the histidine tag comprising the continuous 6 histidine residues and enables affinity purification under neutral buffer conditions.

In this embodiment, these tag peptides are useful for affinity purification or detection of the expressed protein. In addition, the fusion protein with the tag peptide is sometimes increased in expression amount in comparison to natural proteins. The reason is, though not clear, presumably that a complex with an mRNA, ribosome or the like is stabilized at the translation initiation stage to increase translation efficiency.

These tag sequences may contain, in the downstream thereof, a nucleotide sequence that can provide a cleavage site of a protease such as thrombin, Factor Xa or enterokinase, and a desired protein can be purified by being separated from the tag sequences.

Further, it is also possible that the tag sequences are located on the C terminal side of the desired protein and purification can easily be conducted while a function of a leader sequence of the N terminal side remains.

(4) Protein Synthesis Using a Cell-Free Protein Synthesis System

The thus-produced template DNA can synthesize a protein by various methods. For example, it is preferable that a protein is synthesized in a cell-free protein synthesis system. The cell-free protein synthesis system is a system that synthesizes a protein in vitro using a cell extract. As the cell extract, an extract of hitherto-known eukaryotic cells or prokaryotic cells, containing ingredients necessary for protein synthesis, such as ribosome and t-RNA, can be used. A cell extract derived from wheat germ, *Escherichia coli* (for example, *E. coli* S30 cell extract) or *Thermus thermophilus* is preferable because a high synthesis amount is obtained. This *E. coli* S30 cell extract can be produced from *E. coli* A19 (rna met), BL21, BL21 star, BL21 codon plus or the like according to a known method (refer to Pratt. J. M. et al., Transcription and translation—a practical approach, (1984), pp. 179–209, compiled by Henes, B. D. and Higgins, S. J., IRL Press, Oxford), or a product marketed from Promega, Novagen or Roche may be used.

Any of a batchwise method, a flow method and other known techniques can be applied to the cell-free protein synthesis system of the invention. Examples thereof can include a ultrafiltration membrane method, a dialysis membrane method, and a column chromatography method in which a translation template is fixed on a resin (refer to Spirin, A. et al., Meth. In Enzymol. vol. 217, pp. 123–142, 1993).

Besides the cell-free protein synthesis system, it is also possible that, for example, a template DNA is introduced into animal cells through lipofection or the like to express a gene, and a function of the gene product in viable cells is analyzed.

EXAMPLES

In the following Examples of the present invention, the results of expressing, in a cell-free protein synthesis system, human c-Ha-Ras protein, chloramphenicol acetyl transferase (CAT) and various cDNA clones arbitrarily selected from mouse full-length cDNA library (provided from Dr. Hayashizaki Yoshihide, Genome Exploration Research Group, Genomic Sciences Center, RIKEN) are described in detail below. However, the invention is not limited to these Examples.

Example 1

Expression of Ras Protein (1) First PCR

PCR was performed using a linear double-stranded DNA (nucleotide sequence was described in SEQ ID No. 2) coding for Ras protein as a template and three types of primers, 5' primer 1: hRBS>B+6 (SEQ ID. No. 3), 5' primer 2: pRas (SEQ ID No. 4) and 3' primer: p8.2 (SEQ ID No. 5). The composition of the PCR solution and the amplification program were shown in Tables 1 and 2 respectively.

```
5' primer 1: hRBS>B+6 (SEQ ID No. 3)
5'-CCGAAGGAGCCGCCACCAT-3'

5' primer 2: pRas (SEQ ID No. 4)
5'-GAAGGAGCCGCCACCATGACCGAATACAAACTGGTTGTAG-3'

3' PRIMER: p8.2 (SEQ ID No. 5)
5'-GCGGATAACAATTTCACACAGGAAAC-3'
```

TABLE 1

| Composition | Concentration | Amount | Final concentration |
| --- | --- | --- | --- |
| Template plasmid | 1 ng/μl | 4 μl | 0.2 ng/μl |
| 5' Primer 1 (hRBS > B + 6) | 1.6 μM | 1 μl | 0.08 μM |
| 5' Primer 2 | 0.2 μM | 2 μl | 0.02 μM |
| 3' Primer (p8.2) | 2 μM | 1 μl | 0.1 μM |
| dNTPs (Toyobo) | 2 mM | 2 μl | 0.2 mM |
| Expand HF buffer (Boehringer Mannheim) (containing 15 mM magnesium chloride) | (10x) | 2 μl | (1x) |
| Sterile distilled water | | 7.85 μl | |
| DNA polymerase (Boehringer Mannheim) | 3.5 U/μl | 0.15 μl | 0.02625 U/μl |
| Total amount | | 20 μl | |

TABLE 2

| STEP 1 | 94° C. | 2 min |
| --- | --- | --- |
| STEP 2 | 94° C. | 30 sec |
| STEP 3 | 60° C. | 30 sec |
| STEP 4 | 72° C. | 2 min |
| STEP 5 | GOTO 2 for 9 times | |
| STEP 6 | 94° C. | 30 sec |
| STEP 7 | 60° C. | 30 sec |
| STEP 8 | 72° C. | 2 min + 5 sec/cycle |
| STEP 9 | GOTO 6 for 19 times | |
| STEP 10 | 72° C. | 7 min |
| STEP 11 | 4° C. | forever |

(2) Second PCR

Subsequently, the second overlap PCR was performed using the first PCR products obtained in the foregoing reaction, 5' DNA fragment: T7P (one of SEQ ID Nos. 6 to 10) having respective tag sequence in the downstream of the T7 promoter sequence, 3' DNA fragment: T7T (SEQ ID No. 11) having a T7 terminator sequence and universal primer (YA1.2):

5'-GCCGCTGTCCTCGTTCCCAGCC-3' (SEQ ID No. 12).

The composition of the PCR solution and the amplification program were shown in Tables 3 and 2 respectively. Further, the outline of the tag peptides encoded in the 5' DNA fragment used here was shown in Table 4. Consequently, as shown in FIG. 1, a linear double-stranded DNA fragment capable of expressing a fusion protein of various tag sequences and Ras protein was amplified under control of the T7 promoter.

TABLE 3

| Composition | Concentration | Amount | Final concentration |
| --- | --- | --- | --- |
| First PCR product (template) | (×1/5) | 5 μl | (×1/20) |
| Universal primer (YA1.2) | 100 μM | 0.2 μl | 1 μM |
| 5' Fragment (T7P fragment) | 2 nM | 1 μl | 0.1 nM |
| 3' Fragment (T7T fragment) | 2 nM | 1 μl | 0.1 nM |
| dNTPs (Toyobo) | 2 mM | 2 μl | 0.2 mM |
| Expand HF buffer (Boehringer Mannheim) (containing 15 mM magnesium chloride) | (10×) | 2 μl | (1×) |
| Sterile distilled water | | 8.65 μl | |
| DNA polymerase (Boehringer Mannheim) | 3.5 U/μl | 0.15 μl | 0.02625 U/μl |
| Total amount | | 20 μl | |

TABLE 4

| 1 | GST | glutathione-S-transferase |
| --- | --- | --- |
| 2 | MBP | maltose binding protein |
| 3 | TrxA | thioredoxin |
| 4 | CBD | cellulose binding protein |
| 5 | His tag | MKGSSHHHHHH |
| 6 | native His tag | MKDHLIHNVHKEEHAHAHNK |

By the way, with respect to His tag and native His tag, amino acid sequences thereof were shown by one-letter abbreviations.

(3) Protein Synthesis in a Cell-free Protein Synthesis System

*E. coli* S30 extract was prepared from *E. coli* BL21 strain according to a method of Zubay et al. (Annu. Rev. Geneti., 7, 267–287, 1973). With respect to the protein synthesis reaction, Ras protein was synthesized at 37° C. for 1 hour using a 96-well microplate by adding 1 μl of the second PCR products and 7.2 μl of the *E. coli* S30 extract to a solution of a composition shown in Table 5 below in each well thereof to adjust the whole volume of the reaction solution to 30 μl.

TABLE 5

| Composition | Concentration |
| --- | --- |
| HEPES-KOH pH 7.5 | 58.0 mM |
| Dithiothreitol | 2.3 mM |
| ATP | 1.2 mM |
| CTP, GTP, UTP | 0.9 mM each |
| Creatine phosphate | 81.0 mM |
| Creatine kinase | 250.0 μg/ml |
| Polyethylene glycol 8000 | 4.0% |

TABLE 5-continued

| Composition | Concentration |
| --- | --- |
| 3',5'-cAMP | 0.64 mM |
| L(−)-5-formyl-5,6,7,8-tetrahydroforic acid | 35.0 μg/ml |
| *E. coli* total tRNA | 170.0 μg/ml |
| Potassium glutamate | 200.0 mM |
| Ammonium acetate | 27.7 mM |
| Magnesium acetate | 10.7 mM |
| Amino acids | 1.5 mM each |
| T7 RNA polymerase (Toyobo) | 16.0 units/μl |

Example 2

Expression of CAT Protein (1) First PCR

The first PCR was performed in the same manner as in Example 1 using, as a template, a linear double-stranded DNA having a nucleotide sequence described in SEQ ID No. 13 which DNA codes for CAT protein. In this connection, primer pCAT specific for CAT gene and having a nucleotide sequence described in SEQ ID No. 14 was used as 5' primer 2.

```
5' primer 2: pCAT (SEQ ID No. 14)
5'-GAAGGAGCCGCCACCATGGAGAAAAAAATCACTGGATATAC-3'
```

(2) Second PCR and Protein Synthesis in a Cell-Free Protein Synthesis System

The protein was synthesized in a cell-free protein synthesis system after second PCR in the same manner as in Example 1.

Example 3

Expression of Mouse cDNA Clones (1) First PCR

Ten types of cDNA clones optionally selected from mouse full-length cDNA library were used as a template. These are obtained by cloning the respective cDNAs in SacI and XhoI sites of plasmid pBluescriptSK+, and have been registered in GenBank (Accession Nos. are m16206, m21532, x13605, u51204, l16904, s68022, d87663, x65627, m32599 and u85511 respectively). PCR was performed using the common primers in Example 1 as 5' primer 1 and 3' primer and primers specific for the respective cDNAs and having the following nucleotide sequences as 51 primer 2. The composition of the PCR solution and the program were shown in Tables 6 and 2 respectively.

```
5' primer 2: p1A2 (SEQ ID No. 15)
5'-GAAGGAGCCGCCACCATGCTCAAAGTCACGGTGCCC-3'

5' primer 2: p1B2 (SEQ ID No. 16)
5'-GAAGGAGCCGCCACCATGGAGGAGCAGCGCTGTTC-3'

5' primer 2: p1C8 (SEQ ID No. 17)
5'-GAAGGAGCCGCCACCATGGCCCGAACCAAGCAGAC-3'

5' primer 2: p1D2 (SEQ ID No. 18)
5'-GAAGGAGCCGCCACCATGGGTGTTGACAAAATCATTCC-3'

5' primer 2: p1D9 (SEQ ID No. 19)
5'-GAAGGAGCCGCCACCATGTTGGAGACCTACAGCAACC-3'
```

-continued

```
5' primer 2: P1d10 (SEQ ID No. 20)
5'-GAAGGAGCCGCCACCATGGCGGTGCAGGTGGTGC-3'

5' primer 2: p1E4 (SEQ ID No. 21)
5'-GAAGGAGCCGCCACCATGGATGATCGGGAGGATCTG-3'

5' primer 2: P1G4 (SEQ ID No. 22)
5'-GAAGGAGCCGCCACCATGTCGAGTTATTCTAGTGAC-3'

5' primer 2: p1H1 (SEQ ID No. 23)
5'-GAAGGAGCCGCCACCATGGTGAAGGTCGGTGTGAAC-3'

5' primer 2: p1H5 (SEQ ID No. 24)
5'-GAAGGAGCCGCCACCATGGCCAACAGTGAGCG-3'
```

TABLE 6

| Composition | Concentration | Amount | Final concentration |
|---|---|---|---|
| Template plasmid | 0.2 ng/μl | 4 μl | 0.04 ng/μl |
| 5' Primer 1 (hRBS > B + 6) | 10 μM | 1 μl | 0.5 μM |
| 5' Primer 2 | 0.1 μM | 1 μl | 0.005 μM |
| 3' Primer (p8.2) | 10 μM | 1 μl | 0.5 μM |
| dNTPs (Toyobo) | 2 mM | 2 μl | 0.2 mM |
| Expand HF buffer (Boehringer Mannheim) (containing 15 mM magnesium chloride) | (10x) | 2 μl | (1x) |
| Sterile distilled water | | 8.85 μl | |
| DNA polymerase (Boehringer Mannheim) | 3.5 U/μl | 0.15 μl | 0.02625 U/μl |
| Total amount | | 20 μl | |

(2) Second PCR

Second PCR was performed in the same manner as in Example 1. However, regarding the composition of the PCR solution, a reaction solution of a composition shown in Table 7 was used instead of that shown in Table 3.

TABLE 7

| Composition | Concentration | Amount | Final concentration |
|---|---|---|---|
| First PCR product (template) | (×1/10) | 5 μl | (×1/40) |
| Universal primer (YA1.2) | 100 μM | 0.2 μl | 1 μM |
| 5' Fragment (T7P fragment) | 2 nM | 0.5 μl | 0.05 nM |
| 3' Fragment (T7T fragment) | 2 nM | 0.5 μl | 0.05 nM |
| dNTPs (Toyobo) | 2 mM | 2 μl | 0.2 mM |
| Expand HF buffer (Boehringer Mannheim) (containing 15 mM magnesium chloride) | (10x) | 2 μl | (1x) |
| Sterile distilled water | | 9.65 μl | |
| DNA polymerase (Boehringer Mannheim) | 3.5 U/μl | 0.15 μl | 0.02625 U/μl |
| Total amount | | 20 μl | |

Example 4

Confirmation of Synthetic Products

Figure 2:
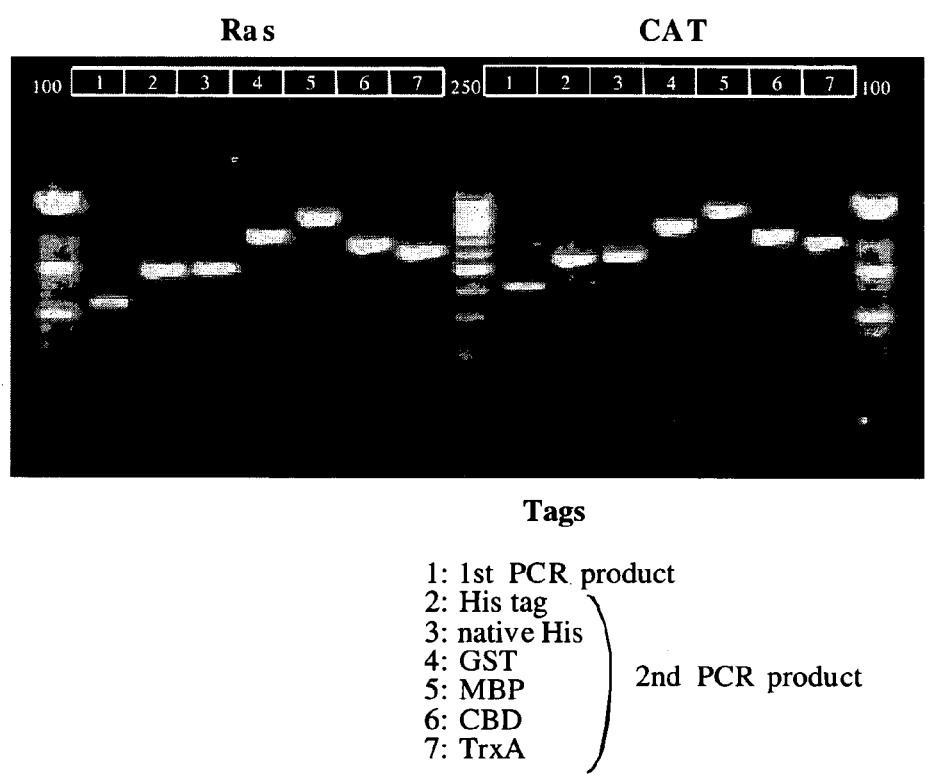
FIG. 2 is a photograph analyzed by agarose gel electrophoresis of samples obtained by PCR amplification of template DNAs coding for Ras and CAT proteins fused with various tag peptides according to the method of the invention.

The results of analyzing by agarose gel electrophoresis a part of the reaction solutions amplified by PCR according to the methods of Examples 1 and 2 were shown in FIG. 2. Lanes 1 to 7 show the following respectively. 1: first PCR products, 2: second PCR products with the addition of His tag, 3: second PCR products with the addition of native His tag, 4: second PCR products with the addition of GST tag, 5: second PCR products with the addition of MBP tag, 6: second PCR products with the addition of CBD tag, and 7: second PCR products with the addition of TrxA tag. It is found that only a single DNA band is detected in both the first PCR and the second PCR and DNAs of correct lengths having bound thereto tag sequences coding for the respective tag peptides are amplified in the second PCR.

Figure 3:
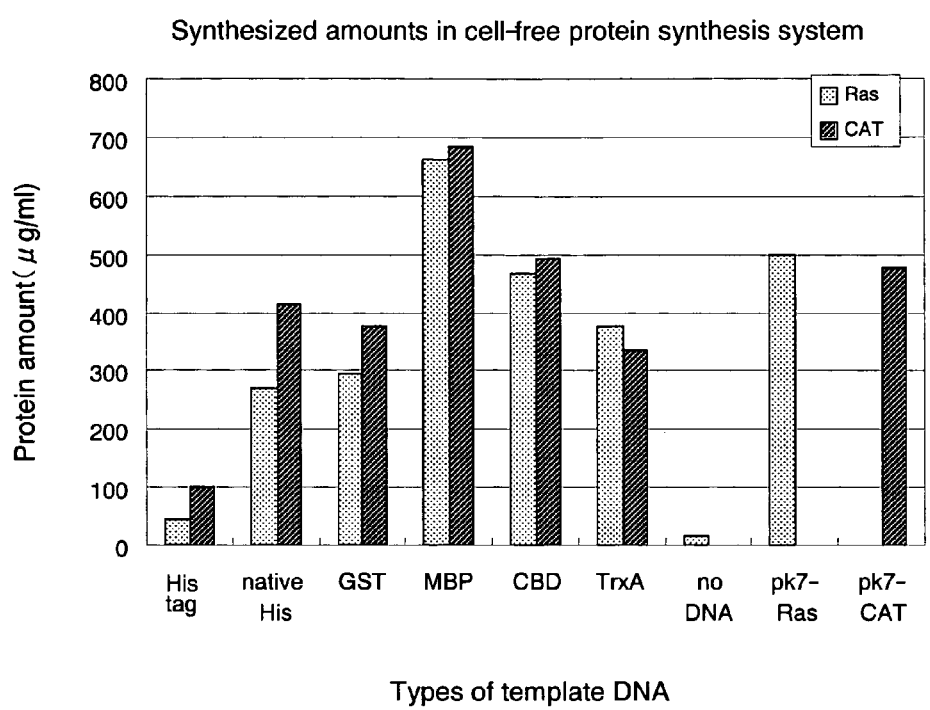
FIG. 3 is a graph showing synthesized amounts of Ras and CAT proteins fused with various tag peptides.

The proteins synthesized in the cell-free synthesis system by the methods of Examples 1 and 2 were quantitatively determined using TOPCOUNT after synthesis in the presence of $^{14}$C labeled Leu. The results were shown in Table 8 below and FIG. 3. Table 8 showed a presumptive molecular weight and an expression amount of Ras protein and CAT protein synthesized as fusion proteins with 6 types of tag peptides. Results of synthesis without the addition of a DNA and results of synthesis in a cell-free protein synthesis system using plasmids pk7-Ras and pk7-CAT (refer to Kigawa et al., FEBS Lett., vol. 442, pp. 15–19, 1999) which are circular double-stranded DNAs were shown as a control. These results revealed that the expression amounts were approximately the same as those in using as a template the circular double-stranded DNA without these tag peptides, though they vary with the types of the tag peptides used.

TABLE 8

| | Ras | | CAT | |
|---|---|---|---|---|
| Tag sequence | Molecular weight (kDa) | Expression amount (μg/ml) | Molecular weight (kDa) | Expression amount (μg/ml) |
| His tag | 22.2 | 45.3 | 28.4 | 99.1 |
| Native His | 20.7 | 268.9 | 29.5 | 413.7 |
| GST | 42.6 | 293.8 | 52.8 | 374.9 |
| MBP | 57.3 | 663.1 | 67.4 | 684.8 |
| CBD | 37.8 | 467.8 | 44.0 | 493.9 |
| TrxA | 28.7 | 375.2 | 38.9 | 335.8 |
| No addition of DNA | — | 14.1 | — | — |
| pk7-Ras | | 498.5 | — | — |
| pk7-CAT | — | — | 28.6 | 478.4 |

Figure 4:
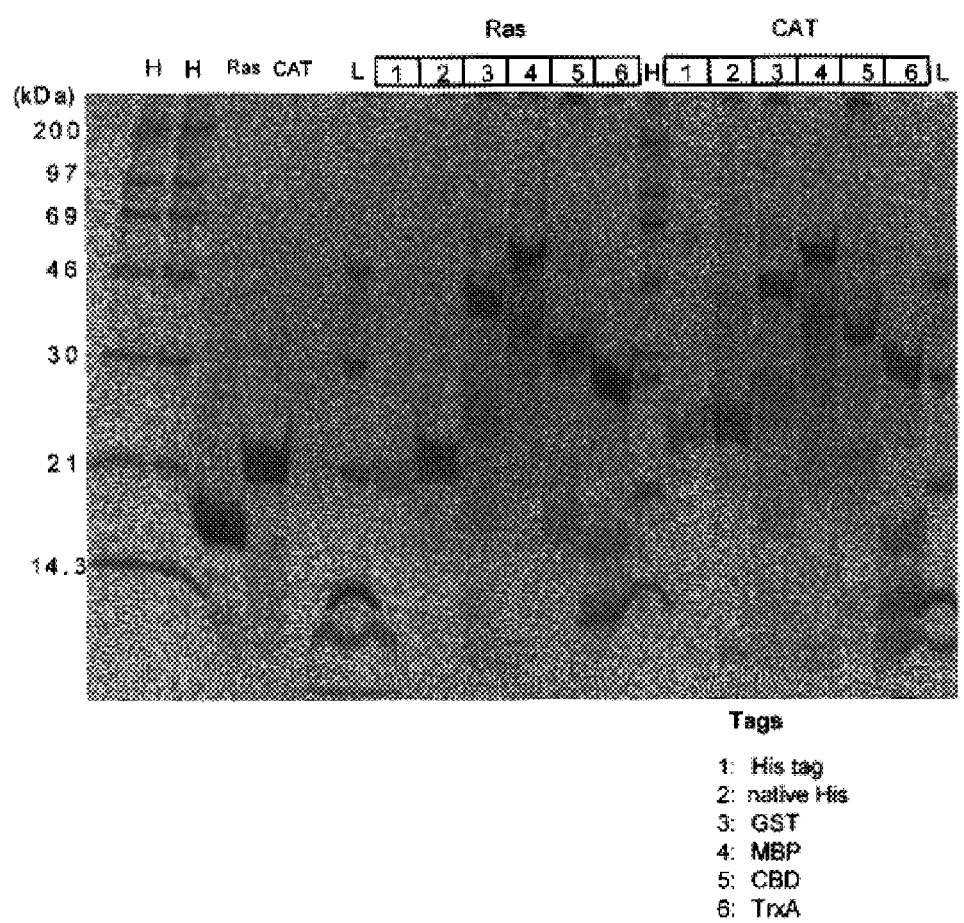
FIG. 4 is a photograph of SDS-PAGE analysis of Ras and CAT proteins and Ras and CAT proteins fused with various tag peptides. Lanes 1 to 6 show respectively; 1—Ras or CAT protein with His tag; 2—Ras or CAT protein with native His tag; 3—Ras or CAT protein with GST tag; 4—Ras or CAT protein with MBP tag; 5—Ras or CAT protein with CBD tag; 6—PAS or CAT protein with TrxA tag. H and L indicate "high" and "low" molecular weight markers.

Further, the results obtained by performing SDS-PAGE using 5 μl of the solution resulting from the protein synthesis in the presence of $^{14}$C-labeled Leu were shown in FIG. 4. In FIG. 4, lanes labeled as 1 to 6 show the following respectively. 1: Ras or CAT protein with the addition of His tag, 2: Ras or CAT protein with the addition of native His tag, 3: Ras or CAT protein with GST tag, 4: Ras or CAT protein with the addition of CBD tag, and 6: Ras or CAT protein with the addition of TrxA tag. In the drawing, in lanes indicated as Ras and CAT, proteins synthesized in a cell-free protein synthesis system using plasmids pk7-Ras and pk7-CAT as a template are shown as a control, and H and L indicate a high-molecular-weight marker and a low-molecular-weight marker respectively. These results indicate that Ras and CAT proteins with the addition of the respective tags are synthesized with correct molecular weights.

Figure 5:
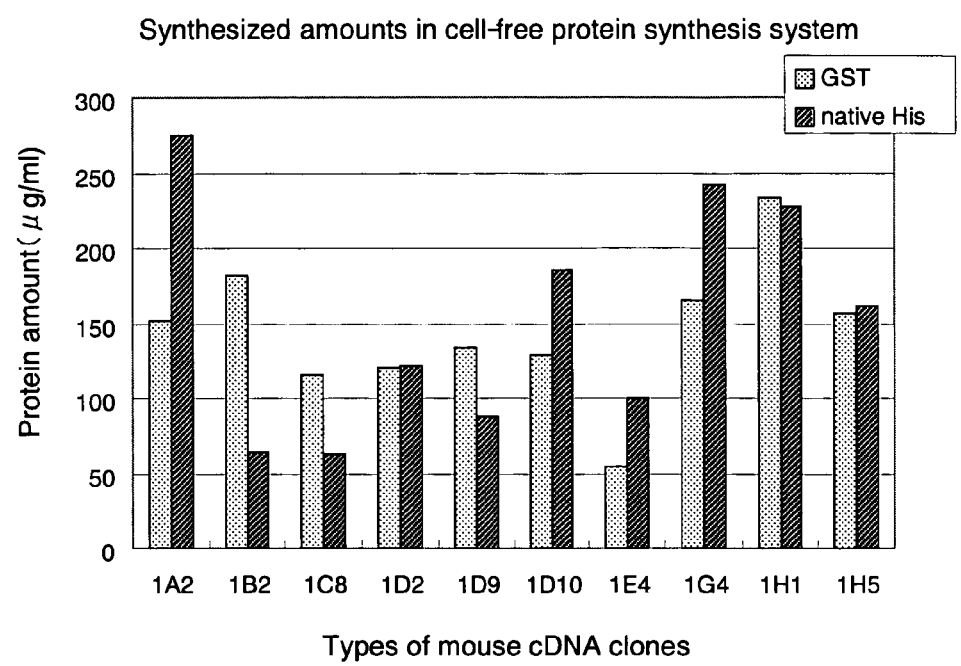
FIG. 5 is a graph showing synthesized amounts of proteins derived from mouse cDNA clones synthesized by fusion with GST and native His tag sequences.

Synthesis amounts of proteins derived from mouse cDNA clones synthesized by fusion with GST and native His tag sequences according to the method in Example 3 were shown in FIG. 5. These results revealed that proteins can be synthesized efficiently from cDNA clones of many samples.

Comparative Example 1

Two-step PCR was performed in the same manner as in Examples 1 and 2 by varying concentrations of the 5' DNA fragment (T7P (GST) or T7P (His tag)) and the 3' DNA fragment (T7T) used in the second PCR. All of the other conditions were the same as in Examples 1 and 2. The results of examining the second PCR products by 1% agarose gel electrophoresis were shown in Table 9.

TABLE 9

| | Sample | | | | | | |
|---|---|---|---|---|---|---|---|
| | 1 | 2 | 3 | 4 | 5 | 6 | 7 |
| Concentrations of T7P and T7T in second PCR solution (pmol/L) | 1 | 5 | 50 | 500 | 2500 | 5000 | 10000 |
| Results of analysis by agarose gel electrophoresis | | | | | | | |
| Ras + GST tag | — | — | ○ | ○ | Δ | Δ | Δ |
| Ras + His tag | — | ○ | ○ | ○ | ○ | Δ | Δ |
| CAT + GST tag | — | ○ | ○ | ○ | Δ | Δ | Δ |
| CAT + His tag | — | ○ | ○ | ○ | ○ | Δ | Δ |
| no DNA + GST tag | — | — | — | — | x | x | x |
| no DNA + His tag | — | — | — | x | x | x | x |

The criteria of the agarose gel electrophoresis are as follows.
—: No PCR product
○: Only correct PCR products are confirmed.
Δ: Both correct PCR products and byproducts are confirmed.
x: Only byproducts are confirmed.

From these results, it is clear that when the respective concentrations of the 5' DNA fragment and the 3' DNA fragment in the second PCR solution are 1 pmol/L, the DNA amplification does not occur, while when the concentrations are 5,000 pmol/L or more, the amounts of byproducts are increased to decrease the purity of the template DNA. Accordingly, it is found that when the respective concentrations of the 5' DNA fragment and the 3' DNA fragment are within the range of from 5 to 2,500 pmol/L, the amplification of the template DNA occurs efficiently.

Comparative Example 2

Two-step PCR was performed in the same manner as in Examples 1 and 2 by varying concentrations of primers used in the first PCR as follows. T7P (GST) and T7P (His tag) were used as the 5' DNA fragment in the second PCR. All of the other conditions were the same as in Examples 1 and 2. The results of examining the second PCR products by 1% agarose gel electrophoresis were shown in Table 10.

TABLE 10

| | Sample | | | | | | |
|---|---|---|---|---|---|---|---|
| | 1 | 2 | 3 | 4 | 5 | 6 | 7 |
| Concentration of primer in first PCR solution (nmol/L) | | | | | | | |
| hRBS > B + 6 primer | 5 | 15 | 40 | 80 | 230 | 480 | 980 |
| pRas or pCAT | 5 | 10 | 10 | 20 | 20 | 20 | 20 |
| p8. 2 primer | 10 | 25 | 50 | 100 | 250 | 500 | 1000 |
| Concentration of primer in second PCR solution (nmol/L) | | | | | | | |
| p8. 2 primer | 0.5 | 1.25 | 2.5 | 5 | 12.5 | 25 | 50 |
| Results of analysis by agarose gel electrophoresis | | | | | | | |
| Ras + GST tag | — | — | ○ | ○ | ○ | x | x |
| Ras + His tag | — | ○ | ○ | ○ | ○ | Δ | Δ |
| CAT + GST tag | — | ○ | ○ | ○ | ○ | x | x |
| CAT + His tag | — | ○ | ○ | ○ | ○ | ○ | Δ |
| no DNA + GST tag | — | — | — | — | x | x | x |
| no DNA + His tag | — | — | — | — | x | x | x |

The criteria of the agarose gel electrophoresis are as follows.
—: No PCR product
○: Only correct PCR products are confirmed.
Δ: Both correct PCR products and byproducts are confirmed.
x: Only byproducts are confirmed.

From these results, it is clear that in the production of the template DNA for expression of Ras and CAT, the amounts of byproducts are increased when the concentration of 3' primer: p8.2 used in the first PCR as an index is 25 nmol/L or more and the amplification of the desired DNA is therefore not conducted. Even when the template DNA was not used as a control, the amplification of only byproducts corresponding to primer dimers was confirmed. Meanwhile, when the concentration of the primer used in the first PCR was 10 nmol/L or less, no efficient DNA amplification was confirmed in the second PCR.

INDUSTRIAL APPLICABILITY

According to the method of the present invention, the template DNA for synthesis, purification and detection of the protein in the cell-free protein synthesis system or the like can be produced rapidly and efficiently on the basis of the cDNA or genomic DNA comprising the sequence coding for the protein. This enables construction of an automated system for the structure and functional analysis of the protein used for study of the Structural Genomics.

The invention claimed is:

1. A method of producing an amplified DNA molecule comprising
   i) amplifying a gene segment of interest by polymerase chain reaction, using a reaction solution comprising:
   a template comprising a first double-stranded or single-stranded DNA fragment cloned in a vector, said DNA fragment comprising a sequence encoding a protein or a portion thereof;
   a first sense primer that anneals with a 5' terminal region of the protein-coding sequence;
   a second sense primer which has a 3' terminal sequence that is the same as at least a 5' portion of the first sense primer and a 5' terminal sequence that is the same as a desired nucleotide sequence; and
   a first anti-sense primer which anneals with a portion of the vector sequence downstream from the protein-coding region; thereby obtaining a first amplified DNA fragment; and
   ii) amplifying the first amplified DNA fragment by polymerase chain reaction, using a reaction solution comprising:
   a) a template mixture comprising
   aa) the first amplified DNA fragment,
   ab) a second double-stranded or single-stranded DNA fragment comprising a sequence hybridizing with the 5' terminal region of the first amplified DNA fragment, and
   ac) a third double-stranded or single-stranded DNA fragment comprising a sequence hybridizing with the 3' terminal region of the first amplified DNA fragment;
   b) a third sense primer which anneals with the 5' terminal region of the second DNA fragment; and
   c) a second anti-sense primer which anneals with the 3' terminal region of the third DNA fragment; wherein the DNA fragment ab) comprises regulatory sequences for transcription and translation of a gene, and the concentrations of the DNA fragments ab) and ac) in the reaction solution ii) each range from 5 to 2,500 pmol/L, thereby obtaining an amplified DNA molecule comprising the overlapped DNA fragments aa), ab) and ac).

2. The method of claim 1, wherein in the amplifying reaction ii) the respective concentrations of the first and second sense primers and of the first antisense primer and the amount of primer dimers produced in the amplifying reaction i) are each less than 20 nmol/L.

3. The method of claim 1, wherein the respective concentrations of primers used for the amplifying reaction i) are from 20 to 500 nmol/L.

4. The method of claim 1, wherein the reaction solution of the amplifying reaction i) comprising the first amplified DNA fragment is diluted 10- to 100-fold before being used in the amplifying reaction ii).

5. The method of claim 1, further comprising a step of removing the first and second sense primers and the first anti-sense primer and primer dimers formed in the amplifying reaction i).

6. The method of claim 1, wherein the amplifying reaction i) is carried out using recombinant microorganisms or a culture broth thereof comprising the template.

7. The method of claim 1, in which the DNA fragment ac) has a 3'-terminal sequence that is the complement of the 5' terminal sequence of the DNA fragment ab) and the sense primer b) is the same as the anti-sense primer c).

8. The method of claim 1, wherein the second DNA fragment and/or the third DNA fragment are single-stranded DNA.

9. The method of claim 1, wherein the third DNA fragment comprises a transcription termination sequence.

10. The method of claim 1, wherein at least one of the second DNA fragment and the third DNA fragment comprises a sequence encoding a tag peptide.

11. The method of claim 1, in which the desired nucleotide sequence of the second sense primer comprises a sequence encoding a tag peptide.

12. The method of claim 10, wherein the tag peptide is maltose binding protein, cellulose binding domain, glutathione-S-transferase, thioredoxin, streptavidin binding peptide or histidine tag peptide.

13. The method of claim 12, wherein the tag peptide is a histidine tag peptide consisting of the amino acid sequence of SEQ ID No. 1.

14. The method of claim 11, wherein the tag peptide is maltose binding protein, cellulose binding domain, glutathione-S-transferase, thioredoxin, streptavidin binding peptide or histidine tag peptide.

15. The method of claim 14, wherein the tag peptide is a histidine tag peptide consisting of the amino acid sequence of SEQ ID No. 1.

* * * * *

SEQUENCE LISTING

<160> NUMBER OF SEQ ID NOS: 25

<210> SEQ ID NO 1
<211> LENGTH: 20
<212> TYPE: PRT

```
<213> ORGANISM: Artificial Sequence
<220> FEATURE:
<223> OTHER INFORMATION: native His tag

<400> SEQUENCE: 1

Met Lys Asp His Leu Ile His Asn Val His Lys Glu Glu His Ala His
 1               5                  10                  15

Ala His Asn Lys
            20

<210> SEQ ID NO 2
<211> LENGTH: 605
<212> TYPE: DNA
<213> ORGANISM: Artificial Sequence
<220> FEATURE:
<223> OTHER INFORMATION: double stranded linear DNA coding for Ras
      protein

<400> SEQUENCE: 2
ggcgtataca tatgaccgaa tacaaactgg ttgtagttgg cgctggtggt gtaggcaaaa      60
gcgcgctgac cattcagttg atccagaacc acttcgtaga tgagtacgac ccgactattg     120
aagactctta ccgtaagcag gttgttatcg acggtgagac ctgtttgctg acatccttg     180 ataccgcagg ccaagaagaa tactctgcta tgcgtgatca gtatatgcgt accggcgaag    240
gcttcctgtg cgttttcgct atcaacaaca ccaaatcttt tgaagacatc catcaatacc    300
gtgaacagat caaacgtgtt aaagactctg atgacgttcc gatggttctg gttggtaaca    360
aatgcgactt ggcagcgcgt actgttgaat ctcgtcaggc tcaggatctg gctcgttctt    420
acggaattcc gtacatcgaa acctctgcta aaactcgtca aggcgttgaa gacgctttct    480
acaccttggt tcgtgaaatc cgtcagcaca agctgcgtaa gctttgatag aattccgtga    540
tagctcgagt cgaccggctg ctaacaaagc ccgaagggt tcctgtgtg aaattgttat     600 ccgct                                                                605

<210> SEQ ID NO 3
<211> LENGTH: 19
<212> TYPE: DNA
<213> ORGANISM: Artificial Sequence
<220> FEATURE:
<223> OTHER INFORMATION: 5' primer-1 universal

<400> SEQUENCE: 3
ccgaaggagc cgccaccat                                                   19

<210> SEQ ID NO 4
<211> LENGTH: 40
<212> TYPE: DNA
<213> ORGANISM: Artificial Sequence
<220> FEATURE:
<223> OTHER INFORMATION: 5' primer-2 for Ras

<400> SEQUENCE: 4
gaaggagccg ccaccatgac cgaatacaaa ctggttgtag                            40

<210> SEQ ID NO 5
<211> LENGTH: 26
<212> TYPE: DNA
<213> ORGANISM: Artificial Sequence
<220> FEATURE:
<223> OTHER INFORMATION: 3' primer universal

<400> SEQUENCE: 5
```

```
gcggataaca atttcacaca ggaaac                                    26
```

<210> SEQ ID NO 6
<211> LENGTH: 844
<212> TYPE: DNA
<213> ORGANISM: Artificial Sequence
<220> FEATURE:
<223> OTHER INFORMATION: 5' DNA fragment comprising GST tag sequence

<400> SEQUENCE: 6

```
ccgctgtcct cgttcccagc ccatgattac gaattcagat ctcgatcccg cgaaattaat    60
acgactcact atagggagac cacaacggtt ccctctaga aataattttg tttaactta   120
agaaggagat atacatatgt cccctatact aggttattgg aaaattaagg gccttgtgca   180
acccactcga cttcttttgg aatatcttga agaaaaatat gaagagcatt tgtatgagcg   240
cgatgaaggt gataaatggc gaaacaaaaa gtttgaattg ggtttggagt ttcccaatct   300
tccttattat attgatggtg atgttaaatt aacacagtct atggccatca tacgttatat   360
agctgacaag cacaacatgt tgggtggttg tccaaaagag cgtgcagaga tttcaatgct   420
tgaaggagcg gttttggata ttagatacgg tgtttcgaga attgcatata gtaaagactt   480
tgaaactctc aaagttgatt ttcttagcaa gctacctgaa atgctgaaaa tgttcgaaga   540
tcgtttatgt cataaaacat atttaaatgg tgatcatgta acccatcctg acttcatgtt   600
gtatgacgct cttgatgttg ttttatacat ggacccaatg tgcctggatg cgttcccaaa   660
attagtttgt tttaaaaaac gtattgaagc tatcccacaa attgataagt acttgaaatc   720
cagcaagtat atagcatggc ctttgcaggg ctggcaagcc acgtttggtg gtggcgacca   780
tcctccaaaa tcggatagct ctggcgcctc cctggtgcca cgcggatccg aaggagccgc   840
cacc                                                             844
```

<210> SEQ ID NO 7
<211> LENGTH: 217
<212> TYPE: DNA
<213> ORGANISM: Artificial Sequence
<220> FEATURE:
<223> OTHER INFORMATION: 5' DNA fragment comprising His tag sequence

<400> SEQUENCE: 7

```
ccgctgtcct cgttcccagc ccatgattac gaattcagat ctcgatcccg cgaaattaat    60
acgactcact atagggagac cacaacggtt ccctctaga aataattttg tttaactta   120
agaaggagat atacatatga aggcagcag ccatcatcat catcatcaca gcagcggcgc   180
ctccctggtg ccacgcggat ccgaaggagc cgccacc                          217
```

<210> SEQ ID NO 8
<211> LENGTH: 244
<212> TYPE: DNA
<213> ORGANISM: Artificial Sequence
<220> FEATURE:
<223> OTHER INFORMATION: 5' DNA fragment comprising native His tag
      sequence

<400> SEQUENCE: 8

```
ccgctgtcct cgttcccagc ccatgattac gaattcagat ctcgatcccg cgaaattaat    60
acgactcact atagggagac cacaacggtt ccctctaga aataattttg tttaactta   120
agaaggagat atacatatga agatcatct catccacaat gtccacaaag aggagcacgc   180
tcatgcccac aacaagagct ctggcgcctc cctggtgcca cgcggatccg aaggagccgc   240
``` cacc                                                                    244

<210> SEQ ID NO 9
<211> LENGTH: 652
<212> TYPE: DNA
<213> ORGANISM: Artificial Sequence
<220> FEATURE:
<223> OTHER INFORMATION: 5' DNA fragment comprising CBD

<400> SEQUENCE: 9
ccgctgtcct cgttcccagc ccatgattac gaattcagat ctcgatcccg cgaaattaat    60
acgactcact atagggagac cacaacggtt tccctctaga ataattttg tttaacttta    120
agaaggagat atacatatgt cagttgaatt ttacaactct aacaaatcag cacaaacaaa    180
ctcaattaca ccaataatca aaattactaa cacatctgac agtgatttaa atttaaatga    240
cgtaaaagtt agatattatt acacaagtga tggtacacaa ggacaaactt tctggtgtga    300
ccatgctggt gcattattag gaaatagcta tgttgataac actagcaaag tgacagcaaa    360
cttcgttaaa gaaacagcaa gcccaacatc aacctatgat acatatgttg aatttggatt    420
tgcaagcgga gcagctactc ttaaaaaagg acaatttata actattcaag gaagaataac    480
aaaatcagac tggtcaaact acactcaaac aaatgactat tcatttgatg caagtagttc    540
aacaccagtt gtaaatccaa aagttacagg atatataggt ggagctaaag ttcttggtac    600
agcaagctct ggcgcctccc tggtgccacg cggatccgaa ggagccgcca cc            652

<210> SEQ ID NO 10
<211> LENGTH: 511
<212> TYPE: DNA
<213> ORGANISM: Artificial Sequence
<220> FEATURE:
<223> OTHER INFORMATION: 5' DNA fragment comprising Thioredoxin sequence

<400> SEQUENCE: 10
ccgctgtcct cgttcccagc ccatgattac gaattcagat ctcgatcccg cgaaattaat    60
acgactcact atagggagac cacaacggtt tccctctaga ataattttg tttaacttta    120
agaaggagat atacatatga gcgataaaat tattcacctg actgacgaca gttttgacac    180
ggatgtactc aaagcggacg gggcgatcct cgtcgatttc tgggcagagt ggtgcggtcc    240
gtgcaaaatg atcgccccga ttctggatga aatcgctgac gaatatcagg gcaaactgac    300
cgttgcaaaa ctgaacatcg atcaaaaccc tggcactgcg ccgaaatatg gcatccgtgg    360
tatcccgact ctgctgctgt tcaaaaacgg tgaagtggcg caaccaaag tgggtgcact    420
gtctaaaggt cagttgaaag agttcctcga cgctaacctg ccagctctg gcgcctccct   480
ggtgccacgc ggatccgaag gagccgccac c                                  511

<210> SEQ ID NO 11
<211> LENGTH: 183
<212> TYPE: DNA
<213> ORGANISM: Artificial Sequence
<220> FEATURE:
<223> OTHER INFORMATION: 3' DNA fragment comprising T7 terminater

<400> SEQUENCE: 11
gtttcctgtg tgaaattgtt atccgctgct gagttggctg ctgccaccgc tgagcaataa   60
ctagcataac cccttggggc ctctaaacgg gtcttgaggg gttttttgct gaaaggagga   120
actatatccg gataacctcg agctgcaggc atgcaagctt ggggctggga acgaggacag   180
cgg                                                                 183

<210> SEQ ID NO 12
<211> LENGTH: 22
<212> TYPE: DNA
<213> ORGANISM: Artificial Sequence
<220> FEATURE:
<223> OTHER INFORMATION: universal primer for 2nd PCR

<400> SEQUENCE: 12
gccgctgtcc tcgttcccag cc                                          22

<210> SEQ ID NO 13
<211> LENGTH: 760
<212> TYPE: DNA
<213> ORGANISM: Artificial Sequence
<220> FEATURE:
<223> OTHER INFORMATION: double stranded linear DNA coding for CAT
      protein

<400> SEQUENCE: 13
ggcgtataca tatggagaaa aaaatcactg gatataccac cgttgatata tcccaatggc    60
atcgtaaaga acattttgag gcatttcagt cagttgctca atgtacctat aaccagaccg   120
ttcagctgga tattacggcc ttttttaaaga ccgtaaagaa aaataagcac aagttttatc   180
cggcctttat tcacattctt gcccgcctga tgaatgctca tccggaattc cgtatggcaa   240
tgaaagacgg tgagctggtg atatgggata gtgttcaccc ttgttacacc gttttccatg   300
agcaaactga aacgttttca tcgctctgga gtgaatacca cgacgatttc cggcagtttc   360
tacacatata ttcgcaagat gtggcgtgtt acggtgaaaa cctggcctat ttccctaaag   420
ggtttattga gaatatgttt ttcgtctcag ccaatccctg ggtgagtttc accagttttg   480
atttaaacgt ggccaatatg gacaacttct tcgcccccgt tttcaccatg ggcaaatatt   540
atacgcaagg cgacaaggtg ctgatgccgc tggcgattca ggttcatcat gccgtctgtg   600
atggcttcca tgtcggcaga atgcttaatg aattacaaca gtactgcgat gagtggcagg   660
gcggggcgta atttttttaa ggcagttatt ggtgcccttaa acgtcgacc ggctgctaac   720 aaagcccgaa agggtttcct gtgtgaaatt gttatccgct                        760

<210> SEQ ID NO 14
<211> LENGTH: 41
<212> TYPE: DNA
<213> ORGANISM: Artificial Sequence
<220> FEATURE:
<223> OTHER INFORMATION: 5' primer-2 for CAT

<400> SEQUENCE: 14
gaaggagccg ccaccatgga gaaaaaaatc actggatata c                      41

<210> SEQ ID NO 15
<211> LENGTH: 36
<212> TYPE: DNA
<213> ORGANISM: Artificial Sequence
<220> FEATURE:
<223> OTHER INFORMATION: 5' primer-2 for 1A2

<400> SEQUENCE: 15
gaaggagccg ccaccatgct caaagtcacg gtgccc                            36

<210> SEQ ID NO 16
<211> LENGTH: 35
<212> TYPE: DNA
<213> ORGANISM: Artificial Sequence

```
<220> FEATURE:
<223> OTHER INFORMATION: 5' primer-2 for 1B2

<400> SEQUENCE: 16
gaaggagccg ccaccatgga ggagcagcgc tgttc                          35

<210> SEQ ID NO 17
<211> LENGTH: 35
<212> TYPE: DNA
<213> ORGANISM: Artificial Sequence
<220> FEATURE:
<223> OTHER INFORMATION: 5' primer-2 for 1C8

<400> SEQUENCE: 17
gaaggagccg ccaccatggc ccgaaccaag cagac                          35

<210> SEQ ID NO 18
<211> LENGTH: 38
<212> TYPE: DNA
<213> ORGANISM: Artificial Sequence
<220> FEATURE:
<223> OTHER INFORMATION: 5' primer-2 for 1D2

<400> SEQUENCE: 18
gaaggagccg ccaccatggg tgttgacaaa atcattcc                       38

<210> SEQ ID NO 19
<211> LENGTH: 37
<212> TYPE: DNA
<213> ORGANISM: Artificial Sequence
<220> FEATURE:
<223> OTHER INFORMATION: 5' primer-2 for 1D9

<400> SEQUENCE: 19
gaaggagccg ccaccatgtt ggagacctac agcaacc                        37

<210> SEQ ID NO 20
<211> LENGTH: 34
<212> TYPE: DNA
<213> ORGANISM: Artificial Sequence
<220> FEATURE:
<223> OTHER INFORMATION: 5' primer-2 for 1D10

<400> SEQUENCE: 20
gaaggagccg ccaccatggc ggtgcaggtg gtgc                           34

<210> SEQ ID NO 21
<211> LENGTH: 36
<212> TYPE: DNA
<213> ORGANISM: Artificial Sequence
<220> FEATURE:
<223> OTHER INFORMATION: 5' primer-2 for 1E4

<400> SEQUENCE: 21
gaaggagccg ccaccatgga tgatcgggag gatctg                         36

<210> SEQ ID NO 22
<211> LENGTH: 36
<212> TYPE: DNA
<213> ORGANISM: Artificial Sequence
<220> FEATURE:
<223> OTHER INFORMATION: 5' primer-2 for 1G4

<400> SEQUENCE: 22
gaaggagccg ccaccatgtc gagttattct agtgac                         36
```

```
<210> SEQ ID NO 23
<211> LENGTH: 36
<212> TYPE: DNA
<213> ORGANISM: Artificial Sequence
<220> FEATURE:
<223> OTHER INFORMATION: 5' primer-2 for 1H1

<400> SEQUENCE: 23
gaaggagccg ccaccatggt gaaggtcggt gtgaac                                    36

<210> SEQ ID NO 24
<211> LENGTH: 32
<212> TYPE: DNA
<213> ORGANISM: Artificial Sequence
<220> FEATURE:
<223> OTHER INFORMATION: 5' primer-2 for 1H5

<400> SEQUENCE: 24
gaaggagccg ccaccatggc caacagtgag cg                                        32

<210> SEQ ID NO 25
<211> LENGTH: 11
<212> TYPE: PRT
<213> ORGANISM: Artificial Sequence
<220> FEATURE:
<223> OTHER INFORMATION: His tag

<400> SEQUENCE: 25

Met Lys Gly Ser Ser His His His His His His
1               5                   10
```